(12) United States Patent
Ueda et al.

(10) Patent No.: US 8,323,195 B2
(45) Date of Patent: Dec. 4, 2012

(54) BLOOD GLUCOSE MEASUREMENT SYSTEM

(75) Inventors: Yasushi Ueda, Ehime (JP); Mamiko Akizuki, Ehime (JP); Hiroyoshi Inoshita, Ehime (JP)

(73) Assignee: Panasonic Corporation, Osaka (JP)

( * ) Notice: Subject to any disclaimer, the term of this patent is extended or adjusted under 35 U.S.C. 154(b) by 846 days.

(21) Appl. No.: 12/347,279

(22) Filed: Dec. 31, 2008

(65) Prior Publication Data
US 2010/0168537 A1 Jul. 1, 2010

(51) Int. Cl.
*A61B 5/00* (2006.01)
*G01N 33/00* (2006.01)

(52) U.S. Cl. ........ 600/365; 600/300; 600/301; 600/319; 600/573; 436/95

(58) Field of Classification Search .......................... None
See application file for complete search history.

(56) References Cited

U.S. PATENT DOCUMENTS

| | | | |
|---|---|---|---|
| 6,066,847 A * | 5/2000 | Rosenthal ................. 250/252.1 |
| 6,269,314 B1 | 7/2001 | Iitawaki et al. |
| 6,309,884 B1 * | 10/2001 | Cooper et al. ................. 436/14 |
| 2007/0231209 A1 * | 10/2007 | Cosentino et al. ........... 422/68.1 |
| 2007/0233395 A1 * | 10/2007 | Neel et al. ......................... 702/19 |
| 2007/0265514 A1 * | 11/2007 | Kiani ............................. 600/316 |
| 2007/0270671 A1 * | 11/2007 | Gal ................................ 600/301 |
| 2009/0036760 A1 * | 2/2009 | Hayter ........................... 600/316 |

FOREIGN PATENT DOCUMENTS

JP 11-56823 3/1999

* cited by examiner

*Primary Examiner* — Samuel Woolwine
(74) *Attorney, Agent, or Firm* — Wenderoth, Lind & Ponack, L.L.P.

(57) ABSTRACT

A blood glucose measurement system in which a blood glucose level measured with an invasive blood glucose measurement apparatus 101 is used to calibrate a blood glucose level measured with a non-invasive blood glucose measurement apparatus 102, comprising a controller that outputs an invasive actuation signal that starts the detection of a characteristic quantity in the body with the invasive blood glucose measurement apparatus, and a blood sampling component for collecting blood from the body on the basis of the invasive actuation signal, wherein measurement with the invasive blood glucose measurement apparatus is begun when the amount of change in the estimated blood glucose level has reached or exceeded a non-invasive blood glucose threshold.

34 Claims, 5 Drawing Sheets

BLOOD GLUCOSE MEASUREMENT SYSTEM

BACKGROUND OF THE INVENTION

1. Field of the Invention

The present invention relates to a blood glucose measurement system that calibrates a blood glucose level measured with a non-invasive blood glucose measurement apparatus by using a blood glucose level measured with an invasive blood glucose measurement apparatus.

2. Description of the Prior Art

The number of patients with diabetes, which is typically a lifestyle disease, is on the rise around the world. Diabetic patients must constantly control their blood glucose level in order to improve their quality of life and to suppress the complications associated with diabetes. To this end, these patients have to measure their blood glucose levels on a regular basis every day under the supervision of a physician.

A common way to measure blood glucose level is to use an invasive type of blood glucose measurement apparatus, which pricks the finger of the patient, collects a blood sample, and measures the blood glucose level. With this invasive blood glucose measurement apparatus, however, pricking the finger to collect a blood sample involves pain and inconvenience, entails the risk of infection, and so forth, and therefore a non-invasive blood glucose measurement apparatus has been proposed that does not require the collection of a blood sample.

With a non-invasive blood glucose measurement apparatus, measuring the absolute concentration of blood glucose is impossible in principle, so the apparatus has to be calibrated using a blood glucose level measured with an invasive blood glucose measurement apparatus. In view of this, a method has been proposed in which a blood glucose level measured with an invasive blood glucose measurement apparatus is stored in a blood glucose level memory on the basis of notification from an invasive blood glucose measurement apparatus and via an information transfer component provided to the non-invasive blood glucose measurement apparatus, the blood glucose level is estimated with a non-invasive blood glucose measurement apparatus, and the blood glucose level estimated by the non-invasive blood glucose measurement apparatus is calibrated using the blood glucose level stored in the blood glucose level memory (see Patent Document 1 (Japanese Laid-Open Patent Publication H11-56823), for example).

SUMMARY OF THE INVENTION

Nevertheless, with the technology discussed in the above-mentioned Patent Document 1, the user has no way to find out if the current blood glucose level measured by the invasive blood glucose measurement apparatus has reached the quantity of information required for calibration. Consequently, measurement has to be performed periodically with an invasive blood glucose measurement apparatus, and even when there is little change in the blood glucose level measured with the invasive blood glucose measurement apparatus, painful blood sample collection is still required periodically.

The present invention solves the problems encountered in the past, and it is an object thereof to provide a blood glucose measurement system in which a blood glucose level measured with an invasive blood glucose measurement apparatus is used to calibrate a blood glucose level measured with a non-invasive blood glucose measurement apparatus, wherein the number of times blood has to be sampled with the invasive blood glucose measurement apparatus is reduced, and the estimated blood glucose level can be displayed during calibration.

To solve the above-mentioned problems encountered in the past, the blood glucose measurement system pertaining to the present invention is one in which a blood glucose level measured with an invasive blood glucose measurement apparatus is used to calibrate a blood glucose level measured with a non-invasive blood glucose measurement apparatus, wherein said blood glucose measurement system comprises an invasive blood glucose measurement apparatus and a non-invasive blood glucose measurement apparatus. The invasive blood glucose measurement apparatus has a blood sampling component and a blood glucose level measurement component. The blood sampling component is for collecting blood from the body on the basis of an invasive measurement command from the non-invasive blood glucose measurement apparatus. The blood glucose level measurement component is for measuring a blood glucose level from blood collected by the blood sampling component. The non-invasive blood glucose measurement apparatus has a controller, a characteristic quantity detector, a blood glucose level estimator, an invasive blood glucose information memory, a blood glucose level calibration calculator, a blood glucose level calibrator, a non-invasive blood glucose level display component, and an invasive measurement command component. The controller outputs a non-invasive actuation signal that instructs the non-invasive blood glucose measurement apparatus to detect a characteristic quantity in the body, and an invasive actuation signal that instructs the invasive blood glucose measurement apparatus to begin measuring a blood glucose level. The characteristic quantity detector detects a characteristic quantity in the body on the basis of the non-invasive actuation signal. The blood glucose level estimator finds an estimated blood glucose level on the basis of the characteristic quantity detected by the characteristic quantity detector. The invasive blood glucose information memory is for storing blood glucose measurement information including a blood glucose level measured by the invasive blood glucose measurement apparatus. The blood glucose level calibration calculator calculates calibration data for calibrating the estimated blood glucose level on the basis of the blood glucose measurement information stored in the invasive blood glucose information memory and the estimated blood glucose level found by the blood glucose level estimator. The blood glucose level calibrator calibrates the estimated blood glucose level found by the blood glucose level estimator on the basis of the calibration data. The non-invasive blood glucose level display component displays the estimated blood glucose level calibrated by the blood glucose level calibrator. The invasive measurement command component receives an invasive measurement command signal outputted from the controller when the amount of change in the estimated blood glucose level during calibration has reached or exceeded a preset non-invasive blood glucose threshold, and instructs the invasive blood glucose measurement apparatus to measure the blood glucose level.

Further, with this blood glucose measurement system, the controller outputs the invasive measurement command signal when the amount of change in the estimated blood glucose level has not reached or exceeded the preset non-invasive blood glucose threshold although a specific length of time has elapsed since the blood glucose level was measured by the invasive blood glucose measurement apparatus.

Further, with this blood glucose measurement system, the controller comprises a register that can be written to from the outside, and the specific length of time can be changed according to the value of said register.

Further, with this blood glucose measurement system, the controller outputs the invasive measurement command signal when the amount of change in the estimated blood glucose level has not reached or exceeded the preset non-invasive blood glucose threshold although measurement has been repeated a specific number of times with the non-invasive blood glucose measurement apparatus since the blood glucose level was measured by the invasive blood glucose measurement apparatus.

Further, with this blood glucose measurement system, the controller comprises a register that can be written to from the outside, and the specific number of times can be changed according to the value of said register.

Further, with this blood glucose measurement system, the blood glucose level estimator comprises a register that can be written to from the outside, and the non-invasive blood glucose threshold can be changed according to the value of said register.

Further, with this blood glucose measurement system, the blood glucose level calibration calculator outputs a processing status signal indicating the conclusion of a calibration period when the amount of change in the blood glucose level measured by the invasive blood glucose measurement apparatus has reached or exceeded a preset invasive blood glucose threshold.

Further, this blood glucose measurement system comprises a register that can be written to from the outside, and the invasive blood glucose threshold can be changed according to the value of said register.

Further, with this blood glucose measurement system, the controller outputs the non-invasive actuation signal on the basis of a preset non-invasive measurement cycle.

Further, with this blood glucose measurement system, the controller comprises a register that can be written to from the outside, and the non-invasive measurement cycle can be changed according to the value of said register.

Further, with this blood glucose measurement system, the controller outputs the invasive measurement command signal when the amount of change in the estimated blood glucose level after calibration has reached or exceeded an abnormal blood glucose threshold.

Further, with this blood glucose measurement system, the blood glucose level estimator comprises a register that can be written to from the outside, and the abnormal blood glucose threshold can be changed according to the value of said register.

Further, with this blood glucose measurement system, the controller counts the number of times that the amount of change in the estimated blood glucose level after calibration has continuously reached or exceeded an abnormal blood glucose threshold, and outputs the invasive measurement command signal when the continuous number of abnormal states has reached or exceeded a continuous abnormal state threshold.

Further, with this blood glucose measurement system, the blood glucose level estimator comprises a register that can be written to from the outside, and the continuous abnormal state threshold can be changed according to the value of said register.

Further, with this blood glucose measurement system, the non-invasive blood glucose measurement apparatus comprises a processing status notification component that notifies the user with a processing status signal, and sends out a processing status signal that is outputted from the blood glucose level calibration calculator and indicates whether or not calibration is in progress.

Further, with this blood glucose measurement system, the processing status notification component notifies the user with sound.

Further, with this blood glucose measurement system, the processing status notification component notifies the user with light.

Further, with this blood glucose measurement system, the processing status notification component notifies the user with vibration.

Further, with this blood glucose measurement system, the processing status notification component notifies the user with a display.

Further, with this blood glucose measurement system, the invasive measurement command component instructs the user about the invasive blood glucose measurement apparatus with sound.

Further, with this blood glucose measurement system, the invasive measurement command component instructs the user about the invasive blood glucose measurement apparatus with light.

Further, with this blood glucose measurement system, the invasive measurement command component instructs the user about the invasive blood glucose measurement apparatus with vibration.

Further, with this blood glucose measurement system, the invasive measurement command component instructs the user about the invasive blood glucose measurement apparatus with a display.

Further, with this blood glucose measurement system, the blood glucose measurement information is the blood glucose levels measured with the blood glucose level measurement component and the timing at which these measurements were made.

Further, with this blood glucose measurement system, the blood glucose measurement information is the blood glucose levels measured with the blood glucose level measurement component, the timing at which these measurements were made, and the temperature at which these measurements were made.

Further, with this blood glucose measurement system, the blood glucose level estimator replaces the non-invasive blood glucose threshold with the invasive blood glucose threshold when the amount of change in a blood glucose level measured with the invasive blood glucose measurement apparatus from a time of 0 minutes has reached or exceeded the non-invasive blood glucose threshold.

Further, with this blood glucose measurement system, the blood glucose level estimator comprises a register that can be written to from the outside, and the function of replacing the non-invasive blood glucose threshold with the invasive blood glucose threshold can be switched on or off according to the value of said register.

Further, with this blood glucose measurement system, the invasive blood glucose measurement apparatus further has an invasive blood glucose level display component that displays the blood glucose level measured by the blood glucose level measurement component. The invasive blood glucose level display component notifies the user of the blood glucose level measured by the blood glucose level measurement component, and the blood glucose level calibration calculator calculates calibration data on the basis of the blood glucose level measured by the blood glucose level measurement component inputted by the user and the estimated blood glucose level found by the blood glucose level estimator.

Further, with this blood glucose measurement system, the invasive blood glucose level display component notifies the user with sound.

Further, with this blood glucose measurement system, the invasive blood glucose level display component notifies the user with light.

Further, with this blood glucose measurement system, the invasive blood glucose level display component notifies the user with vibration.

Further, with this blood glucose measurement system, the invasive blood glucose level display component notifies the user with a display.

Also, with the blood glucose measurement system pertaining to the present invention, the invasive blood glucose measurement apparatus automatically begins measuring the blood glucose level according to a command from the invasive measurement command component of the non-invasive blood glucose measurement apparatus.

The non-invasive blood glucose measurement apparatus of the present invention is one in which a measured non-invasive blood glucose level is calibrated using a blood glucose level measured with an invasive blood glucose measurement apparatus that collects blood from the body and measures the blood glucose level on the basis of an invasive measurement command, said non-invasive blood glucose measurement apparatus comprising a controller, a characteristic quantity detector, a blood glucose level estimator, a blood glucose level calibration calculator, and an invasive measurement command component. The controller outputs a non-invasive actuation signal that instructs the non-invasive blood glucose measurement apparatus to detect a characteristic quantity in the body, and an invasive actuation signal that instructs the invasive blood glucose measurement apparatus to begin measuring a blood glucose level. The characteristic quantity detector detects a characteristic quantity in the body on the basis of the non-invasive actuation signal. The blood glucose level estimator finds an estimated blood glucose level on the basis of the characteristic quantity detected by the characteristic quantity detector and calibration data (discussed below). The blood glucose level calibration calculator calculates calibration data from the blood glucose measurement information, including blood glucose levels, measured by the invasive blood glucose measurement apparatus, and the estimated blood glucose level found by the blood glucose level estimator. The invasive measurement command component receives an invasive measurement command signal outputted from the controller when the amount of change in the estimated blood glucose level during calibration has reached or exceeded a preset non-invasive blood glucose threshold, and instructs the invasive blood glucose measurement apparatus to measure the blood glucose level.

The blood glucose measurement system of the present invention is one in which a blood glucose level measured with an invasive blood glucose measurement apparatus is used to calibrate a blood glucose level measured with a non-invasive blood glucose measurement apparatus, and said blood glucose measurement system comprises an invasive blood glucose measurement apparatus and a non-invasive blood glucose measurement apparatus. The invasive blood glucose measurement apparatus has a blood sampling component and a blood glucose level measurement component. The blood sampling component is for collecting blood from the body on the basis of an invasive measurement command from the non-invasive blood glucose measurement apparatus. The blood glucose level measurement component is for measuring a blood glucose level from blood collected by the blood sampling component. The non-invasive blood glucose measurement apparatus has a controller, a blood glucose level estimator, a blood glucose level calibration calculator, a blood glucose level calibrator, and an invasive measurement command component. The controller outputs a non-invasive actuation signal that instructs the non-invasive blood glucose measurement apparatus to begin measuring a blood glucose level. The blood glucose level estimator finds an estimated blood glucose level for the body on the basis of the non-invasive actuation signal. The blood glucose level calibration calculator calculates calibration data for calibrating the estimated blood glucose level. The blood glucose level calibrator calibrates the estimated blood glucose level found by the blood glucose level estimator on the basis of the calibration data. The invasive measurement command component receives an invasive measurement command signal outputted from the controller when the amount of change in the estimated blood glucose level during calibration has reached or exceeded a preset non-invasive blood glucose threshold, and instructs the invasive blood glucose measurement apparatus to measure the blood glucose level.

DETAILED DESCRIPTION OF THE INVENTION

The blood glucose measurement system pertaining to an embodiment of the present invention will now be described in detail along with the drawings.

Embodiment 1

Figure 1:
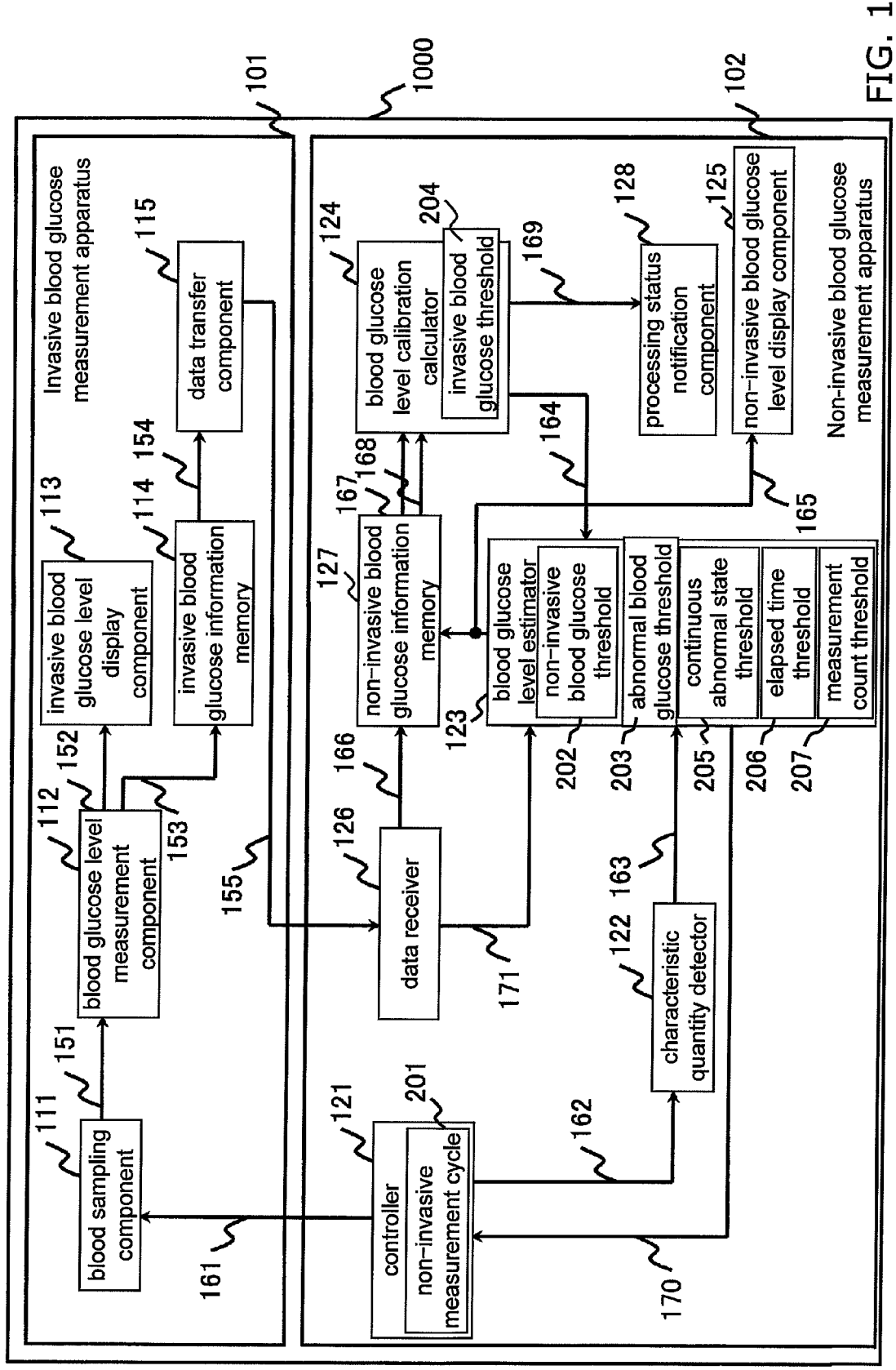
FIG. 1 is a diagram illustrating the configuration of a blood glucose measurement system pertaining to Embodiment 1 of the present invention.

FIG. 1 is a diagram illustrating the configuration of a blood glucose measurement system 1000 pertaining to Embodiment 1.

In FIG. 1, 101 is an invasive blood glucose measurement apparatus, 102 is a non-invasive blood glucose measurement apparatus, 111 is a blood sampling component, 112 is a blood glucose level measurement component, 113 is an invasive blood glucose level display component, 114 is an invasive blood glucose information memory, 115 is a data transfer component, 121 is a controller, 122 is a characteristic quantity detector, 123 is a blood glucose level estimator (blood glucose level estimator, blood glucose level calibrator), 124 is a blood glucose level calibration calculator, 125 is a non-invasive blood glucose level display component, 126 is a data receiver, 127 is a non-invasive blood glucose information memory, 128 is a processing status notification component, 151 is blood, 152 is a blood glucose level, 153 and 154 are blood glucose measurement information, 155 is transferred data, 161 is an invasive actuation signal, 162 is a non-invasive actuation signal, 163 is a characteristic quantity, 164 is calibration data, 165 is an estimated blood glucose level, 166 and 167 are blood glucose measurement information, 168 is an estimated blood glucose level, 169 is a processing status signal, 170 is an invasive measurement request signal, 171 is a reception completion signal, 201 is a non-invasive measurement cycle, 202 is a non-invasive blood glucose threshold, 203 is an abnormal blood glucose threshold, 204 is an invasive blood glucose threshold, 205 is a continuous abnormal state threshold, 206 is an elapsed time threshold, and 207 is a measurement count threshold.

The blood glucose measurement system 1000 in Embodiment 1 is made up of the invasive blood glucose measurement apparatus 101 and the non-invasive blood glucose measurement apparatus 102.

The invasive blood glucose measurement apparatus 101 in Embodiment 1 has the blood sampling component 111, the blood glucose level measurement component 112, the invasive blood glucose level display component 113, the invasive blood glucose information memory 114, and the data transfer component 115. The blood sampling component 111 takes a sample of blood 151 from the body on the basis of the invasive actuation signal 161 from the non-invasive blood glucose measurement apparatus 102. The blood glucose level measurement component 112 measures the blood glucose level 152 from the blood 151 sampled by the blood sampling component 111. The invasive blood glucose level display component 113 displays the blood glucose level 152 measured by the blood glucose level measurement component 112. The invasive blood glucose information memory 114 stores the blood glucose level 152 or other such blood glucose measurement information 153 measured by the blood glucose level measurement component 112. The data transfer component 115 reads the blood glucose measurement information 154 stored in the invasive blood glucose information memory 114, and outputs it as transferred data 155 to the non-invasive blood glucose measurement apparatus 102.

The non-invasive blood glucose measurement apparatus 102 in Embodiment 1 has the controller 121, the characteristic quantity detector 122, the blood glucose level estimator 123, the data receiver 126, the non-invasive blood glucose information memory 127, the blood glucose level calibration calculator 124, the non-invasive blood glucose level display component 125, and the processing status notification component 128. The controller 121 outputs the non-invasive actuation signal 162 that instructs the non-invasive blood glucose measurement apparatus 102 detect a characteristic quantity 163 in the body, and an invasive actuation signal 161 that instructs the invasive blood glucose measurement apparatus to begin measuring a blood glucose level. The characteristic quantity detector 122 detects the characteristic quantity 163 in the body on the basis of the non-invasive actuation signal 162. The blood glucose level estimator 123 finds the estimated blood glucose level 165 from the calibration data 164 and the characteristic quantity 163 detected by the characteristic quantity detector 122. The data receiver 126 receives the transferred data 155 outputted from the data transfer component 115 of the invasive blood glucose measurement apparatus 101. The non-invasive blood glucose information memory 127 stores the blood glucose measurement information 166 included in the transferred data 155 received by the data receiver 126 and the estimated blood glucose level 165 found by the blood glucose level estimator 123. The blood glucose level calibration calculator 124 calculates the calibration data 164 from the estimated blood glucose level 165 found by the blood glucose level estimator 123 and the blood glucose measurement information 167 stored in the non-invasive blood glucose information memory 127. The non-invasive blood glucose level display component 125 displays the estimated blood glucose level 165 found by the blood glucose level estimator 123. The processing status notification component 128 notifies of the processing status signal 169 outputted from the blood glucose level calibration calculator 124.

FIGS. 2A to 2D are graphs in which the blood glucose level 152 and the estimated blood glucose level 165 found by the invasive blood glucose measurement apparatus 101 and the non-invasive blood glucose measurement apparatus 102, respectively, in Embodiment 1 are plotted on the time axis. FIG. 2A shows the blood glucose level 152 and the estimated blood glucose level 165, FIG. 2B the invasive actuation signal 161, FIG. 2C the non-invasive actuation signal 162, and FIG. 2D the invasive measurement request signal 170.

Figure 3:
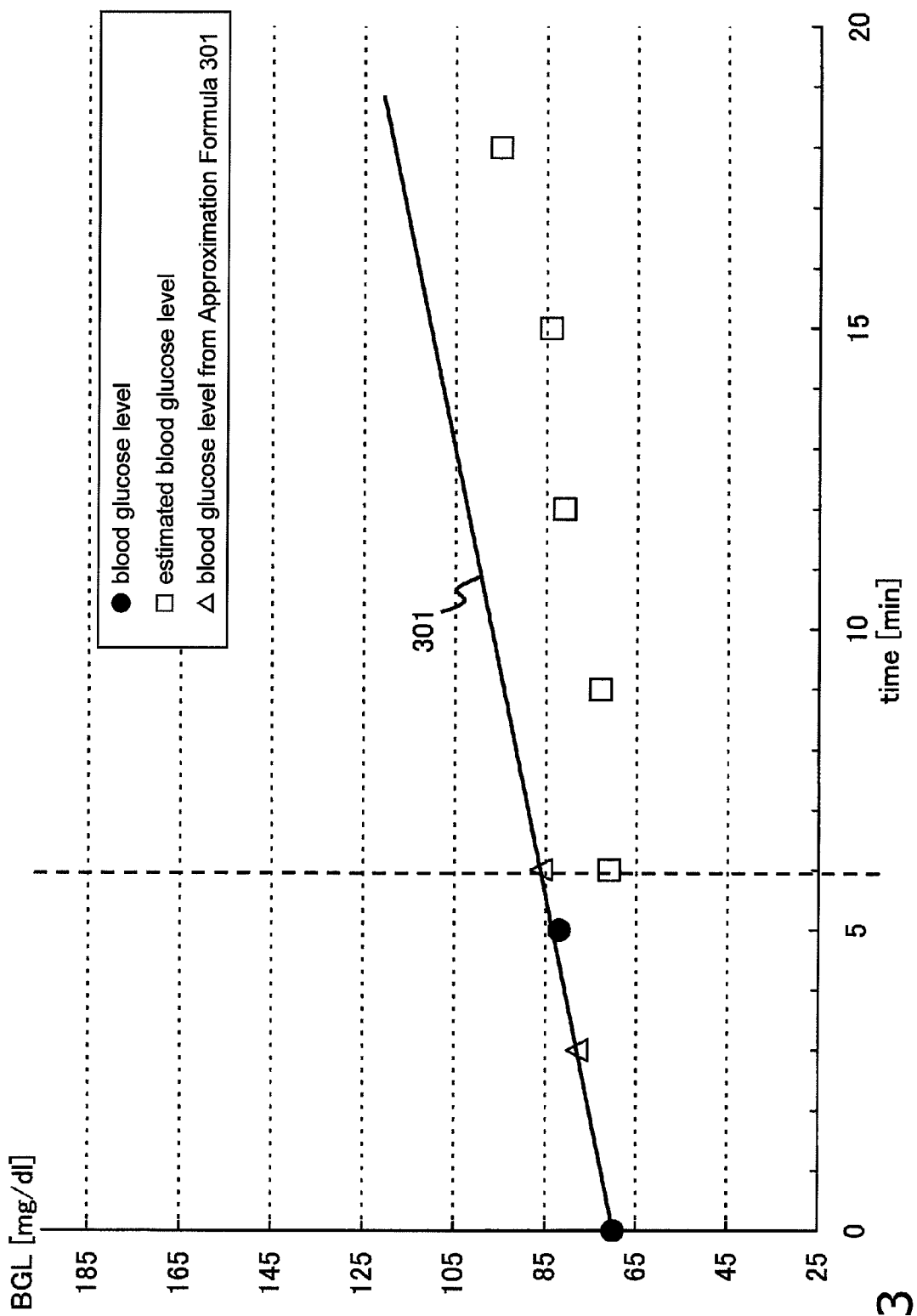
FIG. 3 is an enlargement of from a time of 0 minutes to a time of 20 minutes when the blood glucose level and the estimated blood glucose level in the non-invasive blood glucose measurement apparatus and the invasive blood glucose measurement apparatus in Embodiment 1 of the present invention are plotted on the time axis.

FIG. 3 is an enlargement of from a time of 0 minutes to a time of 20 minutes when the blood glucose level 152 and the estimated blood glucose level 165 in the invasive blood glucose measurement apparatus 101 and the non-invasive blood glucose measurement apparatus 102 in Embodiment 1 are plotted on the time axis. 301 in FIG. 3 is an approximation formula.

Figure 4:
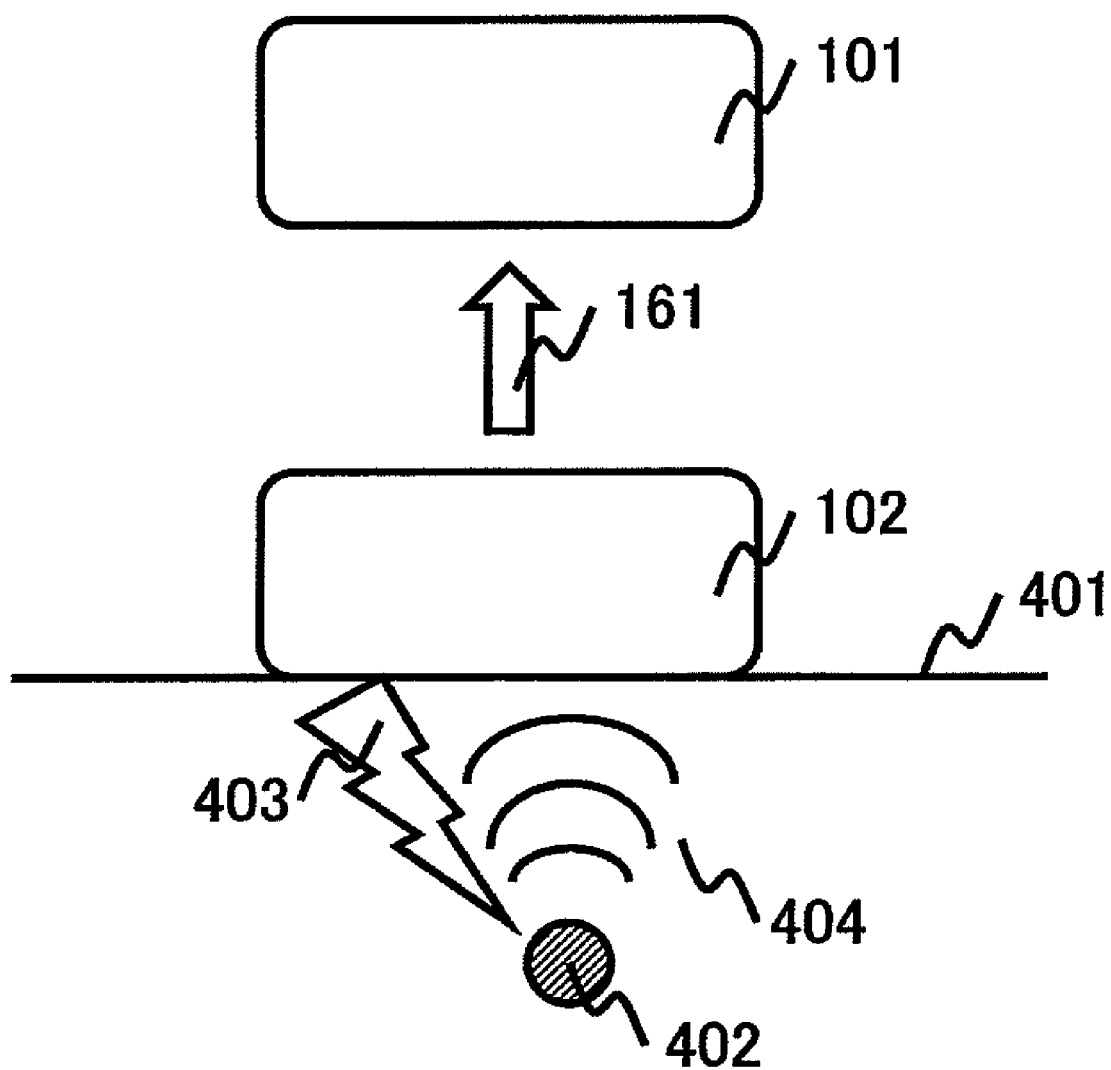
FIG. 4 is a diagram of the system configuration of the invasive blood glucose measurement apparatus and the non-invasive blood glucose measurement apparatus in Embodiment 1 of the present invention.

FIG. 4 is a diagram of the system configuration of the invasive blood glucose measurement apparatus 101 and the non-invasive blood glucose measurement apparatus 102 in Embodiment 1. In FIG. 4, 401 is a body surface, 402 is a vein, 403 is light, and 404 is an photoacoustic wave.

Figure 5A:
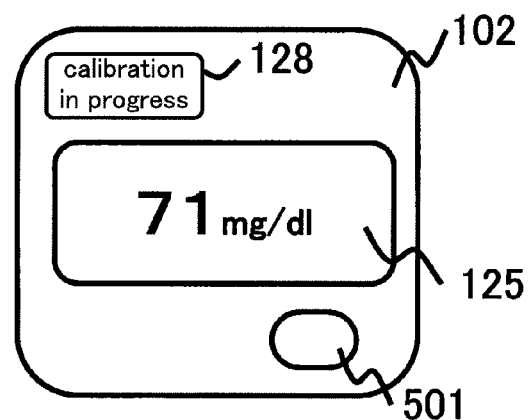
FIGS. 5A to 5C are diagrams illustrating the notification method for the estimated blood glucose level and the processing status signal in the non-invasive blood glucose measurement apparatus in Embodiment 1.
Figure 5B:
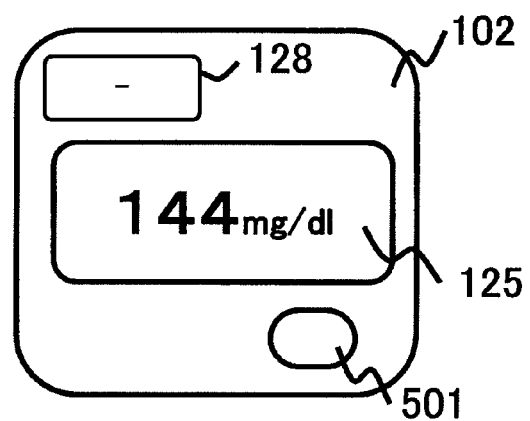
Figure 5C:
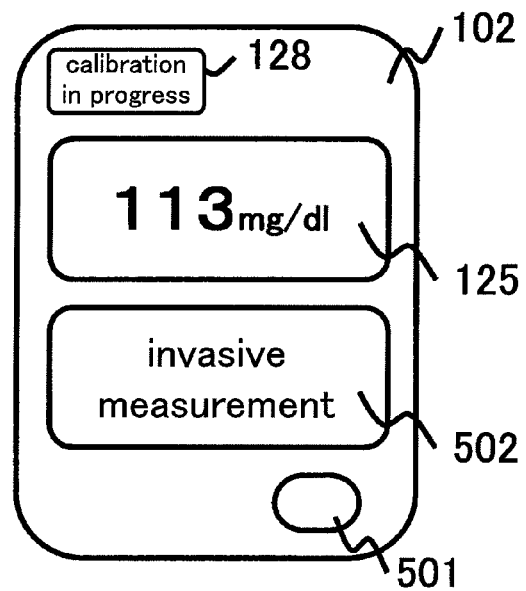

FIGS. 5A to 5C are diagrams illustrating the notification method for the estimated blood glucose level 165 and the processing status signal 169 in the non-invasive blood glucose measurement apparatus 102 in Embodiment 1. In FIGS. 5A to 5C, 501 is a measurement start switch and 502 is an invasive measurement command component.

The operation when the invasive blood glucose measurement apparatus 101 and the non-invasive blood glucose measurement apparatus 102 perform communication will now be described through reference to FIG. 1, FIG. 2, FIG. 3, FIG. 4, and FIGS. 5A to 5C.

The non-invasive blood glucose measurement apparatus 102 here is assumed to be an photoacoustic apparatus, in which the non-invasive measurement cycle 201 is preset as the measurement cycle of the non-invasive blood glucose measurement apparatus 102, the non-invasive blood glucose threshold 202 is preset as the absolute amount of change in the estimated blood glucose level 165 during a calibration period long enough to calculate the calibration data 164 at an accuracy that can be used in a normal measurement period, the abnormal blood glucose threshold 203 is preset as the absolute amount of change in the estimated blood glucose level 165 during a normal measurement period, the invasive blood glucose threshold 204 is preset as the absolute amount of change from a time of 0 minutes in the blood glucose level measured by the invasive blood glucose measurement apparatus 101, the continuous abnormal state threshold 205 is preset as the continuous number of times the amount of change in the estimated blood glucose level 165 during a normal measurement period has reached or exceeded the abnormal blood glucose threshold 203, and the elapsed time threshold 206 is preset as the time it takes for the amount of change in the estimated blood glucose level 165 to exceed the non-invasive blood glucose threshold 202 from the timing at which the blood glucose level was measured in the invasive blood glucose measurement apparatus 101. Here, the non-invasive measurement cycle 201 is set to 3 minutes, the non-invasive blood glucose threshold 202 to 65 mg/dl, the abnormal blood glucose threshold 203 to 25 mg/dl, the invasive blood glucose threshold 204 to 65 mg/dl, the continuous abnormal state threshold 205 to one time, and the elapsed time threshold 206 to 20 minutes.

The measurement cycle of the invasive blood glucose measurement apparatus 101 is approximately 5-minute intervals, and the blood glucose measurement information 154 includes the measurement timing and the blood glucose level 152 measured by the blood glucose level measurement component 112.

First, at a time of 0 minutes, the invasive actuation signal 161 is outputted when a blood sampling switch (not shown) provided to the invasive blood glucose measurement apparatus 101 is pressed by the user. The blood 151 is collected from the body when the invasive actuation signal 161 is detected by the blood sampling component 111, which is a puncture needle or the like.

The blood glucose level measurement component 112 measures the blood glucose level 152 from the collected blood 151.

The measured blood glucose level 152 is displayed on the invasive blood glucose level display component 113, and is stored along with the measurement time in the invasive blood glucose information memory 114.

Let us say that the blood glucose level 152 at a time of 0 minutes is 70 mg/dl.

The data transfer component 115 reads the blood glucose measurement information at a time of 0 minutes stored in the invasive blood glucose information memory 114, and outputs this as the transferred data 155.

The data receiver 126 receives the transferred data 155 outputted from the data transfer component 115, and stores the blood glucose measurement information 166 from the transferred data 155 in the non-invasive blood glucose information memory 127. The data receiver 126 then outputs the reception completion signal 171 to the blood glucose level estimator 123.

The blood glucose level estimator 123 begins measurement of the blood glucose level upon detection of the reception completion signal 171, and measures how long it takes for the amount of change in the estimated blood glucose level 165 to exceed the non-invasive blood glucose threshold 202.

The non-invasive blood glucose measurement apparatus 102 is placed on the body surface 401, such as an arm, and the measurement start switch 501 of the non-invasive blood glucose measurement apparatus 102 is pressed. The controller 121 outputs the non-invasive actuation signal 162 when it detects that the measurement start switch 501 has been pressed.

What is being described here is that measurement is begun in the invasive blood glucose measurement apparatus 101 and the non-invasive blood glucose measurement apparatus 102 simultaneously when the user presses the blood sampling switch and the measurement start switch 501, respectively. However, the measurement need not be carried out at the same time, and measurement may instead be begun by actuating first the invasive blood glucose measurement apparatus 101 and then the non-invasive blood glucose measurement apparatus 102. Or, measurement may be begun by actuating first the non-invasive blood glucose measurement apparatus 102 and then the invasive blood glucose measurement apparatus 101.

The light 403 propagates through the body and is absorbed by substances in the vein 402 that allow the blood glucose level to be estimated, and the photoacoustic wave 404 is produced.

The characteristic quantity detector 122 begins detection of the photoacoustic wave 404 on the basis of the non-invasive actuation signal 162, and detects and stores the characteristic quantity 163.

At a time of 3 minutes, the non-invasive blood glucose measurement apparatus 102 performs measurements at 3-minute intervals according to the non-invasive measurement cycle 201 preset. The controller 121 shines the light 403 on the body surface 401, and outputs the non-invasive actuation signal 162 to the characteristic quantity detector 122.

The light 403 propagates through the body and is absorbed by substances in the vein 402 that allow the blood glucose level to be estimated. The photoacoustic wave 404 is produced at this point.

The characteristic quantity detector 122 begins detection of the photoacoustic wave 404 on the basis of the non-invasive actuation signal 162, and detects and stores the characteristic quantity 163.

The elapsed time at this point is 3 minutes.

At a time of 5 minutes, just as at a time of 0 minutes, the user presses the blood sampling switch provided to the invasive blood glucose measurement apparatus 101, whereupon measurement is commenced by the invasive blood glucose measurement apparatus 101. The measurement method here is the same as at a time of 0 minutes.

Let us say that the blood glucose level 152 at this point is 82 mg/dl.

The data transfer component 115 reads the blood glucose measurement information for the time of 5 minutes stored in the invasive blood glucose information memory 114, and outputs it as transferred data 155.

The data receiver 126 receives the transferred data 155 outputted from the data transfer component 115, and stores the blood glucose measurement information 166 from the transferred data 155 in the non-invasive blood glucose information memory 127. The data receiver 126 then outputs the reception completion signal 171 to the blood glucose level estimator 123.

Upon detection of the reception completion signal 171, the blood glucose level estimator 123 resets the elapsed time that has been counted up to that point, and starts over measuring the time it takes until the amount of change in the estimated blood glucose level 165 exceeds the non-invasive blood glucose threshold 202.

At a time of 6 minutes, just as at a time of 3 minutes, measurement is commenced in the non-invasive blood glucose measurement apparatus 102. At this point the characteristic quantity 163 is detected by the characteristic quantity detector 122 by detecting the photoacoustic wave generated when the light 403 is absorbed by substances in the vein 402 that allow the blood glucose level to be estimated.

At this point there are two pieces of data for the invasive blood glucose measurement apparatus 101 (70 mg/dl at a time of 0 minutes, and 82 mg/dl at a time of 5 minutes). Therefore, the blood glucose level calibration calculator 124 finds the Approximation Formula 301 based on these data, calculates an approximate blood glucose level ($\Delta$ in FIG. 3), and calculates the calibration data 164 based on the characteristic quantity 163 at times of 0, 3, and 6 minutes in the non-invasive blood glucose measurement apparatus 102 and this approximate blood glucose level. The blood glucose level calibration calculator 124 then outputs the temporary calibration data 164 thus calculated to the blood glucose level estimator 123, and outputs the processing status signal 169, which indicates that calibration is in progress, to the processing status notification component 128.

The elapsed time at this point is 1 minute.

The blood glucose level estimator 123 finds the estimated blood glucose level 165 (71 mg/dl) at a time of 6 minutes on the basis of the calibration data 164, and outputs this to the non-invasive blood glucose level display component 125 (FIG. 5A). The blood glucose level estimator 123 also finds the difference between the estimated blood glucose level 165 at a time of 6 minutes and the blood glucose level (70 mg/dl) of the invasive blood glucose measurement apparatus 101 at a time of 0 minutes, and calculates the amount of change (1 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

What was described here was a method in which the blood glucose level of the invasive blood glucose measurement apparatus 101 at times of 3 and 6 minutes was calculated from the Approximation Formula 301 at a time of 6 minutes, but it is also possible to perform calibration by calculating at a time of 5 minutes the approximate non-invasive characteristic quantity at a time of 5 minutes with an approximation formula from the characteristic quantity at times of 0 and 3 minutes.

At a time of 9 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 4 minutes.

The blood glucose level estimator 123 finds the difference between the estimated blood glucose level at a time of 9 minutes (73 mg/dl) and the blood glucose level of the invasive blood glucose measurement apparatus 101 at a time of 0 minutes, and calculates the amount of change (3 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 12 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 7 minutes.

The blood glucose level estimator 123 finds the difference between the estimated blood glucose level at a time of 12 minutes (81 mg/dl) and the blood glucose level of the invasive blood glucose measurement apparatus 101 at a time of 0 minutes, and calculates the amount of change (11 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 15 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 10 minutes.

The blood glucose level estimator 123 finds the difference between the estimated blood glucose level at a time of 15 minutes (84 mg/dl) and the blood glucose level of the invasive blood glucose measurement apparatus 101 at a time of 0 minutes, and calculates the amount of change (14 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 18 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 13 minutes.

The blood glucose level estimator 123 finds the difference between the estimated blood glucose level at a time of 18 minutes (95 mg/dl) and the blood glucose level of the invasive blood glucose measurement apparatus 101 at a time of 0 minutes, and calculates the amount of change (25 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 21 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 16 minutes.

The blood glucose level estimator 123 finds the difference between the estimated blood glucose level at a time of 21 minutes (102 mg/dl) and the blood glucose level of the invasive blood glucose measurement apparatus 101 at a time of 0 minutes, and calculates the amount of change (32 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 24 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 19 minutes.

The blood glucose level estimator 123 finds the difference between the estimated blood glucose level at a time of 24 minutes (100 mg/dl) and the blood glucose level of the invasive blood glucose measurement apparatus 101 at a time of 0 minutes, and calculates the amount of change (30 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 27 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 22 minutes.

The blood glucose level estimator 123 finds the difference between the estimated blood glucose level at a time of 27 minutes (108 mg/dl) and the blood glucose level of the invasive blood glucose measurement apparatus 101 at a time of 0 minutes, and calculates the amount of change (38 mg/dl).

Here, the amount of change in the estimated blood glucose level does not exceed the non-invasive blood glucose threshold 202, but the elapsed time exceeds the elapsed time threshold 206. Thus, the blood glucose level estimator 123 decides that an amount of change in the blood glucose level that would be sufficient to calibrate the estimated blood glucose level within the elapsed measurement time has not been obtained, and outputs to the controller 121 the invasive measurement request signal 170 that requests measurement with the invasive blood glucose measurement apparatus 101.

The controller 121 produces the invasive actuation signal 161 on the basis of the invasive measurement request signal 170, and outputs it to the invasive blood glucose measurement apparatus 101.

The blood sampling component 111 collects the blood 151 from the body upon detection of the invasive actuation signal 161 outputted from the controller 121.

The blood glucose level measurement component 112 measures the blood glucose level 152 for the collected blood 151.

The measured blood glucose level 152 is displayed on the invasive blood glucose level display component 113, and is stored along with the measurement time in the invasive blood glucose information memory 114.

Let us say that the blood glucose level 152 at this point is 100 mg/dl.

The data transfer component 115 reads the blood glucose measurement information at a time of 28 minutes stored in the invasive blood glucose information memory 114, and outputs this as the transferred data 155.

The data receiver 126 receives the transferred data 155 outputted from the data transfer component 115, stores the blood glucose measurement information 166 from the transferred data 155 in the non-invasive blood glucose information memory 127, and outputs the reception completion signal 171 to the blood glucose level estimator 123.

Upon detection of the reception completion signal 171, the blood glucose level estimator 123 resets the elapsed time that has been counted up to that point, and starts over measuring the time it takes until the amount of change in the estimated blood glucose level 165 exceeds the non-invasive blood glucose threshold 202.

The blood glucose level calibration calculator 124 finds an approximation formula from the blood glucose measurement information 167 for three times stored in the non-invasive blood glucose information memory 127 (in FIG. 2, black circles for 0 minutes and 5 minutes, and a black diamond for 28 minutes), and calculates approximate invasive blood glucose levels from 6 minutes to 27 minutes. These approximate invasive blood glucose levels are then used to calculate temporary calibration data 164, and the temporary calibration data 164 are outputted to the blood glucose level estimator 123. Also, the difference between the blood glucose level at a time of 27 minutes (100 mg/dl) and the blood glucose level of the invasive blood glucose measurement apparatus 101 at a time of 0 minutes is found, and the amount of change in the invasive blood glucose level (30 mg/dl) is calculated. Since the amount of change in this invasive blood glucose level does not exceed the invasive blood glucose threshold 204, the processing status signal 169, which indicates that calibration is still in progress, is outputted to the processing status notification component 128.

The blood glucose level estimator 123 finds the estimated blood glucose level 165 (x in FIG. 2) after the application of temporary calibration data at a time of 28 minutes on the basis of the temporary calibration data 164, and outputs this to the non-invasive blood glucose level display component 125.

At a time of 30 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 3 minutes.

The blood glucose level estimator 123 finds the difference between the estimated blood glucose level at a time of 30 minutes (113 mg/dl) and the blood glucose level of the invasive blood glucose measurement apparatus 101 at a time of 0 minutes, and calculates the amount of change (43 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 33 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 6 minutes.

The blood glucose level estimator 123 finds the difference between the estimated blood glucose level at a time of 33 minutes (121 mg/dl) and the blood glucose level of the invasive blood glucose measurement apparatus 101 at a time of 0 minutes, and calculates the amount of change (51 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 36 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 9 minutes.

The blood glucose level estimator 123 finds the difference between the estimated blood glucose level at a time of 36 minutes (125 mg/dl) and the blood glucose level of the invasive blood glucose measurement apparatus 101 at a time of 0 minutes, and calculates the amount of change (55 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 39 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 12 minutes.

The blood glucose level estimator 123 finds the difference between the estimated blood glucose level at a time of 39 minutes (138 mg/dl) and the blood glucose level of the invasive blood glucose measurement apparatus 101 at a time of 0 minutes, and calculates the amount of change (68 mg/dl). Since the amount of change here has reached or exceeded the non-invasive blood glucose threshold 202, the blood glucose level estimator 123 decides that an amount of change in the blood glucose level that would be sufficient to calibrate the estimated blood glucose level has been obtained, and outputs to the controller 121 the invasive measurement request signal 170 that requests measurement with the invasive blood glucose measurement apparatus 101.

Here, the blood glucose level estimator 123 was described as calculating as the amount of change the difference between the estimated blood glucose level at various measurement times and the blood glucose level of the invasive blood glucose measurement apparatus 101 at a measurement time of 0 minutes, and comparing this with the non-invasive blood glucose threshold 202. However, it is also possible to add the difference from the estimated blood glucose level measured with the non-invasive blood glucose measurement apparatus 102 one time earlier (three minutes earlier), and compare this value with the non-invasive blood glucose threshold 202.

The controller 121 produces the invasive actuation signal 161 on the basis of the invasive measurement request signal 170, and outputs it to the invasive blood glucose measurement apparatus 101.

The blood sampling component 111 collects the blood 151 from the body upon detection of the invasive actuation signal 161 outputted from the controller 121.

The blood glucose level measurement component 112 measures the blood glucose level 152 for the collected blood 151.

The measured blood glucose level 152 is displayed on the invasive blood glucose level display component 113, and is stored along with the measurement time in the invasive blood glucose information memory 114.

Let us say that the blood glucose level 152 at this point is 110 mg/dl.

The data transfer component 115 reads the blood glucose measurement information at a time of 40 minutes stored in the invasive blood glucose information memory 114, and outputs this as the transferred data 155.

The data receiver 126 receives the transferred data 155 outputted from the data transfer component 115, stores the blood glucose measurement information 166 from the transferred data 155 in the non-invasive blood glucose information memory 127, and outputs the reception completion signal 171 to the blood glucose level estimator 123.

Upon detection of the reception completion signal 171, the blood glucose level estimator 123 resets the elapsed time that has been counted up to that point, and starts over measuring the time it takes until the amount of change in the estimated blood glucose level 165 exceeds the non-invasive blood glucose threshold 202.

The blood glucose level calibration calculator 124 finds an approximation formula from the blood glucose measurement information 167 for four times stored in the non-invasive blood glucose information memory 127 (in FIG. 2, black circles for 0 minutes and 28 minutes, and black diamonds for 28 minutes and 40 minutes), and calculates approximate invasive blood glucose levels from 6 minutes to 39 minutes. These approximate invasive blood glucose levels are then used to calculate temporary calibration data 164, and the temporary calibration data 164 are outputted to the blood glucose level estimator 123. Also, the difference between the blood glucose level at a time of 39 minutes (110 mg/dl) and the blood glucose level of the invasive blood glucose measurement apparatus 101 at a time of 0 minutes is found, and the amount of change in the invasive blood glucose level (40 mg/dl) is calculated. Since the amount of change in this invasive blood glucose level does not exceed the invasive blood glucose threshold 204, the processing status signal 169, which indicates that calibration is still in progress, is outputted to the processing status notification component 128.

The blood glucose level estimator 123 finds the estimated blood glucose level 165 (x in FIG. 2) after the application of temporary calibration data at a time of 40 minutes on the basis of the temporary calibration data 164, and outputs this to the non-invasive blood glucose level display component 125.

At a time of 42 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 3 minutes.

The blood glucose level estimator 123 finds the difference between the estimated blood glucose level at a time of 42 minutes (127 mg/dl) and the blood glucose level of the invasive blood glucose measurement apparatus 101 at a time of 0 minutes, and calculates the amount of change (57 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 45 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 6 minutes.

The blood glucose level estimator 123 finds the difference between the estimated blood glucose level at a time of 45 minutes (130 mg/dl) and the blood glucose level of the invasive blood glucose measurement apparatus 101 at a time of 0 minutes, and calculates the amount of change (60 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 48 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 9 minutes.

The blood glucose level estimator 123 finds the difference between the estimated blood glucose level at a time of 48 minutes (132 mg/dl) and the blood glucose level of the invasive blood glucose measurement apparatus 101 at a time of 0 minutes, and calculates the amount of change (62 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 51 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 12 minutes.

The blood glucose level estimator 123 finds the difference between the estimated blood glucose level at a time of 51 minutes (137 mg/dl) and the blood glucose level of the invasive blood glucose measurement apparatus 101 at a time of 0 minutes, and calculates the amount of change (67 mg/dl). Since the amount of change here has reached or exceeded the non-invasive blood glucose threshold 202, the blood glucose level estimator 123 decides that an amount of change in the blood glucose level that would be sufficient to calibrate the estimated blood glucose level has been obtained, and outputs to the controller 121 the invasive measurement request signal 170 that requests measurement with the invasive blood glucose measurement apparatus 101.

The controller 121 produces the invasive actuation signal 161 on the basis of the invasive measurement request signal 170, and outputs it to the invasive blood glucose measurement apparatus 101.

The blood sampling component 111 collects the blood 151 from the body upon detection of the invasive actuation signal 161 outputted from the controller 121.

The blood glucose level measurement component 112 measures the blood glucose level 152 for the collected blood 151.

The measured blood glucose level 152 is displayed on the invasive blood glucose level display component 113, and is stored along with the measurement time in the invasive blood glucose information memory 114.

Let us say that the blood glucose level 152 at this point is 125 mg/dl.

The data transfer component 115 reads the blood glucose measurement information at a time of 52 minutes stored in the invasive blood glucose information memory 114, and outputs this as the transferred data 155.

Here, the data transfer component 115 was described as reading the blood glucose measurement information 154 for the invasive blood glucose measurement apparatus 101 measured at a time of 51 minutes, and outputting it as the transferred data 155. However, all of the blood glucose measurement information 154 measured in the past may instead be compiled and outputted together as the transferred data 155.

The data receiver 126 receives the transferred data 155 outputted from the data transfer component 115, stores the blood glucose measurement information 166 from the transferred data 155 in the non-invasive blood glucose information memory 127, and outputs the reception completion signal 171 to the blood glucose level estimator 123.

Upon detection of the reception completion signal 171, the blood glucose level estimator 123 resets the elapsed time that has been counted up to that point, and starts over measuring the time it takes until the amount of change in the estimated blood glucose level 165 exceeds the non-invasive blood glucose threshold 202.

Figure 2:
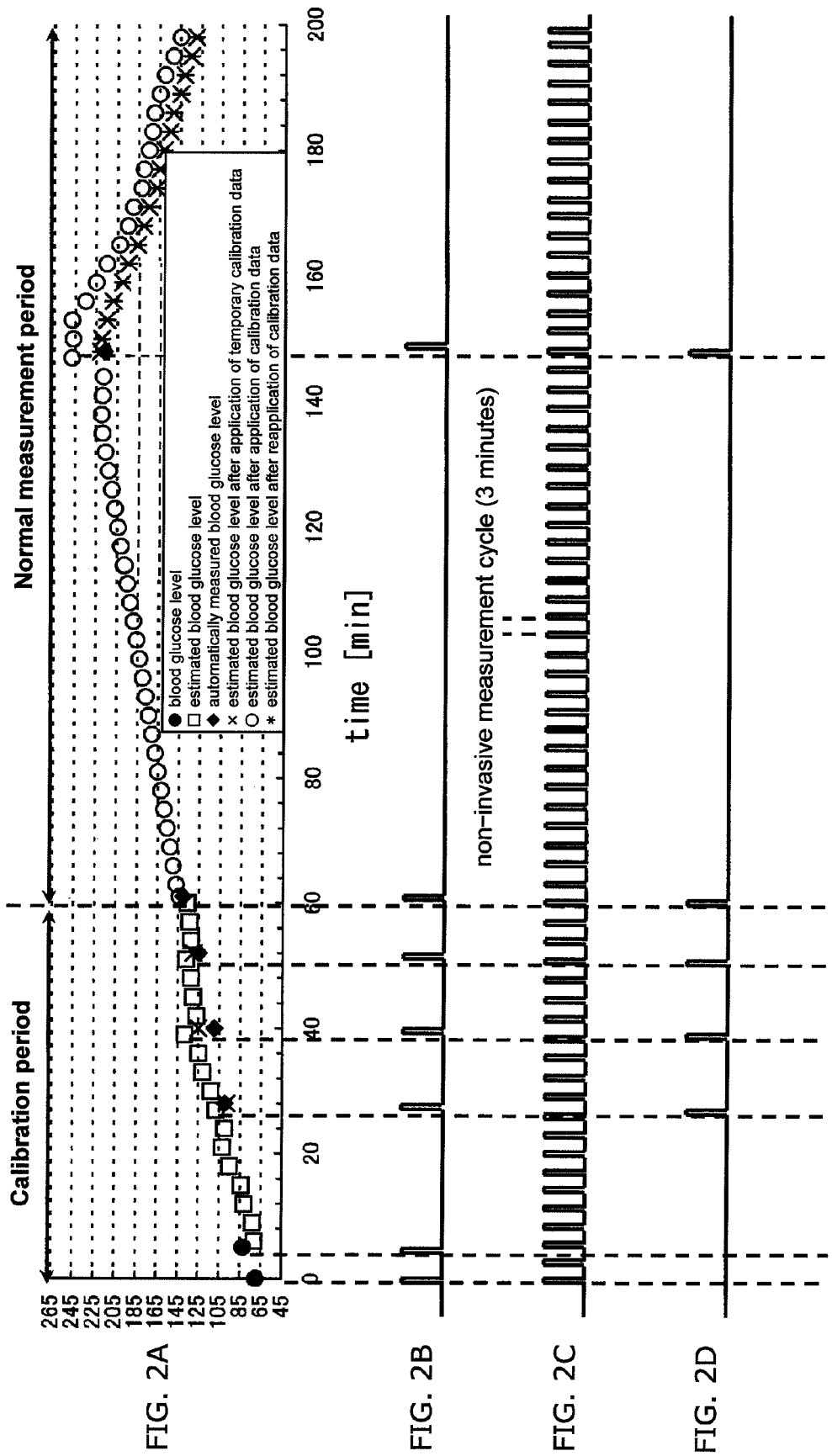
FIGS. 2A to 2D are graphs in which the blood glucose level and the estimated blood glucose level found by the invasive blood glucose measurement apparatus and the non-invasive blood glucose measurement apparatus, respectively, in Embodiment 1 of the present invention are plotted on the time axis.

The blood glucose level calibration calculator 124 finds an approximation formula from the blood glucose measurement information 167 for five times stored in the non-invasive blood glucose information memory 127 (in FIG. 2, black circles for 0 minutes and 5 minutes, and black diamonds for 28 minutes, 40 minutes, and 52 minutes). The blood glucose level calibration calculator 124 then calculates approximate invasive blood glucose levels from 6 minutes to 51 minutes. These approximate invasive blood glucose levels are then used to calculate temporary calibration data 164, and the temporary calibration data 164 are outputted to the blood glucose level estimator 123. Also, the difference between the blood glucose level at a time of 52 minutes (125 mg/dl) and the blood glucose level of the invasive blood glucose measurement apparatus 101 at a time of 0 minutes is found, and the amount of change in the invasive blood glucose level (55 mg/dl) is calculated. Since the amount of change in this invasive blood glucose level does not exceed the invasive blood glucose threshold 204, the processing status signal 169, which indicates that calibration is still in progress, is outputted to the processing status notification component 128.

The blood glucose level estimator 123 finds the estimated blood glucose level 165 (x in FIG. 2) after the application of temporary calibration data at a time of 52 minutes on the basis of the temporary calibration data 164, and outputs this to the non-invasive blood glucose level display component 125 (FIG. 5A).

At a time of 54 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 3 minutes.

The blood glucose level estimator 123 finds the difference between the estimated blood glucose level at a time of 54 minutes (132 mg/dl) and the blood glucose level of the invasive blood glucose measurement apparatus 101 at a time of 0 minutes, and calculates the amount of change (62 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 57 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 6 minutes.

The blood glucose level estimator 123 finds the difference between the estimated blood glucose level at a time of 57 minutes (134 mg/dl) and the blood glucose level of the invasive blood glucose measurement apparatus 101 at a time of 0 minutes, and calculates the amount of change (64 mg/dl). Since the elapsed time here does not exceed the elapsed time threshold 206, and the amount of change in the estimated blood glucose level does not exceed the non-invasive blood glucose threshold 202, no actuation command is sent to the invasive blood glucose measurement apparatus 101.

At a time of 60 minutes, just as at a time of 3 minutes, measurement is commenced in the non-invasive blood glucose measurement apparatus 102, and the estimated blood glucose level 165 is stored in the non-invasive blood glucose information memory 127.

The elapsed time at this point is 9 minutes.

The blood glucose level estimator 123 finds the difference between the estimated blood glucose level at a time of 60 minutes (136 mg/dl) and the blood glucose level of the invasive blood glucose measurement apparatus 101 at a time of 0 minutes, and calculates the amount of change (66 mg/dl). Since the amount of change here has reached or exceeded the non-invasive blood glucose threshold 202, the blood glucose level estimator 123 decides that an amount of change in the blood glucose level that would be sufficient to calibrate the estimated blood glucose level has been obtained, and outputs to the controller 121 the invasive measurement request signal 170 that requests measurement with the invasive blood glucose measurement apparatus 101.

The controller 121 produces the invasive actuation signal 161 on the basis of the invasive measurement request signal 170, and outputs it to the invasive blood glucose measurement apparatus 101.

The blood sampling component 111 collects the blood 151 from the body upon detection of the invasive actuation signal 161 outputted from the controller 121.

The blood glucose level measurement component 112 measures the blood glucose level 152 for the collected blood 151.

The measured blood glucose level 152 is displayed on the invasive blood glucose level display component 113, and is stored along with the measurement time in the invasive blood glucose information memory 114.

Let us say that the blood glucose level 152 at this point is 140 mg/dl.

The data transfer component 115 reads the blood glucose measurement information at a time of 61 minutes stored in the invasive blood glucose information memory 114, and outputs this as the transferred data 155.

The data receiver 126 receives the transferred data 155 outputted from the data transfer component 115, stores the blood glucose measurement information 166 from the transferred data 155 in the non-invasive blood glucose information memory 127, and outputs the reception completion signal 171 to the blood glucose level estimator 123.

Upon detection of the reception completion signal 171, the blood glucose level estimator 123 resets the elapsed time that has been counted up to that point, and starts over measuring the time it takes until the amount of change in the estimated blood glucose level 165 exceeds the non-invasive blood glucose threshold 202.

The blood glucose level calibration calculator 124 finds an approximation formula from the blood glucose measurement information 167 for six times stored in the non-invasive blood glucose information memory 127 (in FIG. 2, black circles for 0 minutes and 5 minutes, and black diamonds for 28 minutes, 40 minutes, 52 minutes, and 61 minutes). The blood glucose level calibration calculator 124 then calculates approximate invasive blood glucose levels from 6 minutes to 60 minutes. The blood glucose level calibration calculator 124 then uses these approximate invasive blood glucose levels to calculate temporary calibration data 164, and the temporary calibration data 164 are outputted to the blood glucose level estimator 123. Also, the difference between the blood glucose level at a time of 61 minutes (140 mg/dl) and the blood glucose level of the invasive blood glucose measurement apparatus 101 at a time of 0 minutes is found, and the amount of change in the invasive blood glucose level (70 mg/dl) is calculated. Since the amount of change in this invasive blood glucose level here has reached or exceeded the invasive blood glucose threshold 204, the processing status signal 169, which indicates the conclusion of a calibration period, is outputted to the processing status notification component 128.

The blood glucose level estimator 123 finds the estimated blood glucose level 165 (white circles in FIG. 2) after the application of calibration data at a time of 61 minutes on the basis of the calibration data 164, and outputs this to the non-invasive blood glucose level display component 125 (FIG. 5B).

When the calibration period ends, the normal measurement period begins, and the controller 121 shines the light 403 on the body surface 401 every 3 minutes from a time of 63 minutes onward. Also, the characteristic quantity detector 122 commences the detection of the photoacoustic wave 404 generated from substances in the vein 402 that allow the blood glucose level to be estimated, and detects the characteristic quantity 163, on the basis of the non-invasive actuation signal 162 outputted to the characteristic quantity detector 122. The blood glucose level estimator 123 then finds the estimated blood glucose level 165 after the application of calibration data on the basis of the calibration data 164 from the detected characteristic quantity 163, and the series of processing steps displayed by the non-invasive blood glucose level display component 125 is the same as in the calibration period.

At a time of 60 minutes, the blood glucose level estimator 123 finds the difference between the estimated blood glucose level at a time of 61 minutes (144 mg/dl) and the estimated blood glucose level at a time of 63 minutes (147 mg/dl), and calculates the amount of change in the estimated blood glucose level 165 (3 mg/dl). Since the amount of change in the estimated blood glucose level 165 here does not exceed the abnormal blood glucose threshold 203, the invasive measurement request signal 170 is not outputted.

Just as at a time of 63 minutes, the light 403 is emitted every three minutes from a time of 66 minutes to a time of 144 minutes at a command from the controller 121. The blood glucose level estimator 123 carries out a series of processing in which the estimated blood glucose level 165 is found, the amount of change in the estimated blood glucose level 165 is calculated, this is compared with the abnormal blood glucose threshold 203, and the estimated blood glucose level 165 is displayed on the non-invasive blood glucose level display component 125. At this point, since the amount of change in the measured estimated blood glucose level 165 does not exceed the abnormal blood glucose threshold 203 at the various measurement times, the invasive measurement request signal 170 is not outputted.

At a time of 147 minutes, the light 403 is emitted at a command from the controller 121. The blood glucose level estimator 123 then finds the estimated blood glucose level 165, finds the difference between the estimated blood glucose level at a time of 147 minutes (248 mg/dl) and the estimated blood glucose level at a time of 144 minutes (218 mg/dl), and calculates the amount of change in the estimated blood glucose level 165 (30 mg/dl). At this point the amount of change in the estimated blood glucose level 165 has reached or exceeded the abnormal blood glucose threshold 203, and the continuous abnormal state threshold 205 is one time. Thus, the blood glucose level estimator 123 decides that abnormal data has been detected, and outputs to the controller 121 the invasive measurement request signal 170 that requests measurement with the invasive blood glucose measurement apparatus 101.

The controller 121 produces the invasive actuation signal 161 on the basis of the invasive measurement request signal 170, and outputs it to the invasive blood glucose measurement apparatus 101.

The blood sampling component 111 collects the blood 151 from the body upon detection of the invasive actuation signal 161 outputted from the controller 121.

The blood glucose level measurement component 112 measures the blood glucose level 152 for the collected blood 151.

The measured blood glucose level 152 is displayed on the invasive blood glucose level display component 113, and is stored along with the measurement time in the invasive blood glucose information memory 114.

Let us say that the blood glucose level 152 at this point is 217 mg/dl.

The data transfer component 115 reads the blood glucose measurement information at a time of 148 minutes stored in the invasive blood glucose information memory 114, and outputs this as the transferred data 155.

The data receiver 126 receives the transferred data 155 outputted from the data transfer component 115, and stores the blood glucose measurement information 166 from the transferred data 155 in the non-invasive blood glucose information memory 127.

The blood glucose level calibration calculator 124 finds an approximation formula from the blood glucose measurement information 167 for six times stored in the non-invasive blood glucose information memory 127 (in FIG. 2, black circles for 0 minutes and 5 minutes, and black diamonds for 40 minutes, 52 minutes, 61 minutes, and 148 minutes). The blood glucose level calibration calculator 124 then recalculates the calibration data 164, and outputs this calculated calibration data 164 to the blood glucose level estimator 123.

The blood glucose level estimator 123 finds the estimated blood glucose level 165 (* in FIG. 2) after the application of calibration data at a time of 148 minutes on the basis of the calculated calibration data 164, and outputs this to the non-invasive blood glucose level display component 125.

Just as at a time of 63 minutes, every 3 minutes from a time of 150 minutes onward the blood glucose level estimator 123 finds the difference between the estimated blood glucose level at a time of 150 minutes (220 mg/dl) and the estimated blood glucose level at a time of 148 minutes (221 mg/dl), and calculates the amount of change in the estimated blood glucose level 165 (−1 mg/dl). Here, since the amount of change in the estimated blood glucose level 165 does not exceed the abnormal blood glucose threshold 203, the invasive measurement request signal 170 is not outputted.

Thus, with the blood glucose measurement system pertaining to Embodiment 1, the difference is found between the estimated blood glucose level 165 measured using the temporary calibration data 164 and the blood glucose level 152 of the invasive blood glucose measurement apparatus 101. As a result, the controller 121 provided to the non-invasive blood glucose measurement apparatus 102 outputs the invasive actuation signal 161 and recommends blood sampling with the invasive blood glucose measurement apparatus 101, thereby reducing the unnecessary blood sampling that occurred when measurements were made in a regular cycle.

Also, in Embodiment 1, by providing the processing status notification component 128, the user can be notified that calibration is in progress, and the estimated blood glucose level 165 can be displayed although the final accuracy has not yet been attained. Thus it is possible to notify the condition in the apparatus to the user.

Also, in Embodiment 1, by calculating the amount of change in the estimated blood glucose level 165 after the calibration period, it is determined that abnormal data has been generated when the amount of change in the estimated blood glucose level 165 has reached or exceeded the abnormal blood glucose threshold 203. Thus, it is possible to recommend measurement with the invasive blood glucose measurement apparatus 101, and even after the calibration period, the calibration data 164 can be recalculated and the abnormal data subjected to revision.

Also, in Embodiment 1, the non-invasive blood glucose measurement apparatus 102 was described as assuming an apparatus that made use of photoacoustic waves, but may instead be another apparatus for invasively finding a blood glucose level, and the same effects as above will be obtained.

Also, in Embodiment 1, the blood glucose measurement information 154 was the blood glucose level 152 measured with the blood glucose level measurement component 112, and the timing at which these measurements were made, but the blood glucose measurement information 154 can also include as additional information the temperature at the point when the blood glucose level 152 was measured with the blood glucose level measurement component 112, which will further improve the accuracy of the estimated blood glucose level 165.

Also, in Embodiment 1, the description assumed that measurement with the invasive blood glucose measurement apparatus 101 was performed by outputting the invasive actuation signal 161 from the controller 121, but if the invasive measurement command component 502 (FIG. 5C) is provided, the user can be notified of measurement with the invasive blood glucose measurement apparatus 101, and the invasive blood glucose measurement apparatus 101 may be actuated at a command from the invasive measurement command component 502. Here again, the same effects as above are obtained.

Also, in Embodiment 1, a case was described in which the blood glucose level measured with the invasive blood glucose measurement apparatus 101 was transmitted to the non-invasive blood glucose measurement apparatus 102 by the transferred data 155 outputted from the data transfer component 115, but the configuration may instead be such that the user reads the blood glucose level displayed by the invasive blood glucose level display component 113, and uses a data input component (not shown) instead of the data receiver 126 to transfer the blood glucose level to the non-invasive blood glucose measurement apparatus. Here again, the same effects as above are obtained.

Also, how the user is notified of the blood glucose level by the invasive blood glucose level display component 113 may be such that notification of the blood glucose level is performed by a transfer method (encoding rule) in which determined between the user and the invasive blood glucose level display component 113 ahead of time.

Also, in Embodiment 1, a case was described in which the blood glucose level estimator 123 was equipped with the elapsed time threshold 206, and after the blood glucose level was measured with the invasive blood glucose measurement apparatus 101, the invasive blood glucose measurement apparatus 101 was told to begin measurement of the blood glucose level when the amount of change in the estimated blood glucose level did not reach or exceed the non-invasive blood glucose threshold 202 even after a specific amount of time had elapsed. However, by providing the measurement count threshold 207, the invasive blood glucose measurement apparatus 101 may be told to begin measurement of the blood glucose level when, after the blood glucose level has first been measured with the invasive blood glucose measurement apparatus 101, the amount of change in the estimated blood glucose level does not reach or exceed the non-invasive blood glucose threshold 202 even after measurement with the non-invasive blood glucose measurement apparatus 102 has been repeated a specific number of times. Here again, the same effects as above are obtained.

With the blood glucose measurement system of the present invention, even during calibration, the estimated blood glucose level can be displayed although the final accuracy has not yet been attained, and the number of unnecessary blood samplings can be reduced by recommending blood sampling with an invasive blood glucose measurement apparatus whenever the measurement accuracy of the estimated blood glucose level drops to the point that the amount of change in the blood glucose level required to perform calibration is obtained.

Furthermore, abnormal data can be revised after the calibration period by recommending blood sampling with an invasive blood glucose measurement apparatus when abnormal data is produced in the estimated blood glucose level after the calibration period.

With the blood glucose measurement system of the present invention, the number of unnecessary blood samplings can be reduced by recommending blood sampling with an invasive blood glucose measurement apparatus when the amount of change in the blood glucose level required to perform calibration is exceeded the predetermined point because of reducing the accuracy of the estimated blood glucose level.

INDUSTRIAL APPLICABILITY

The blood glucose measurement system pertaining to the present invention reduces unnecessary blood sampling by actuating an invasive blood glucose measurement apparatus in a state in which the measurement accuracy of the estimated blood glucose level has yet to reach the final accuracy and yields an amount of change in the blood glucose level required to perform calibration is obtained, and this reduces pain and inconvenience on the part of the user and lowers the risk of infection and so forth.

What is claimed is:

1. A blood glucose measurement system comprising:
an invasive blood glucose measurement apparatus; and
a non-invasive blood glucose measurement apparatus;
wherein the invasive blood glucose measurement apparatus includes:
a blood sampling component that collects blood from the body on the basis of an invasive measurement command from the non-invasive blood glucose measurement apparatus; and
a blood glucose level measurement component that measures a blood glucose level from blood collected by the blood sampling component,
wherein the non-invasive blood glucose measurement apparatus calibrates a measured blood glucose level by using a blood glucose level measured with the invasive blood glucose measurement apparatus,
wherein the non-invasive blood glucose measurement apparatus has:
a controller that outputs a non-invasive actuation signal that instructs the non-invasive blood glucose measurement apparatus to detect a characteristic quantity in the body, and an invasive actuation signal that instructs the invasive blood glucose measurement apparatus to begin measuring a blood glucose level;
a characteristic quantity detector that detects the characteristic quantity in the body on the basis of the non-invasive actuation signal;
a blood glucose level estimator that finds an estimated blood glucose level on the basis of the characteristic quantity detected by the characteristic quantity detector;
an invasive blood glucose information memory that stores blood glucose measurement information including a blood glucose level measured by the invasive blood glucose measurement apparatus;
a blood glucose level calibration calculator that calculates calibration data for calibrating the estimated blood glucose level on the basis of the blood glucose measurement information stored in the invasive blood glucose information memory and the estimated blood glucose level found by the blood glucose level estimator;
a blood glucose level calibrator that calibrates the estimated blood glucose level found by the blood glucose level estimator on the basis of the calibration data;
a non-invasive blood glucose level display component that displays the estimated blood glucose level calibrated by the blood glucose level calibrator; and
an invasive measurement command component that receives the invasive actuation signal outputted from the controller and instructs the invasive blood glucose measurement apparatus to measure the blood glucose level,
wherein the controller outputs the invasive actuation signal when the difference between the estimated blood glucose level and the blood glucose level measured by the invasive blood glucose measurement apparatus during calibration has reached or exceeded a preset non-invasive blood glucose threshold.

2. The blood glucose measurement system according to claim 1,
wherein the blood glucose level estimator comprises a register that can be written to from the outside, and the non-invasive blood glucose threshold can be changed according to the value of said register.

3. The blood glucose measurement system according to claim 1,
wherein the blood glucose level calibration calculator outputs a processing status signal indicating the conclusion of a calibration period when the amount of change in the blood glucose level measured by the invasive blood glucose measurement apparatus has reached or exceeded a preset invasive blood glucose threshold.

4. The blood glucose measurement system according to claim 3,
further comprising a register that can be written to from the outside, and the invasive blood glucose threshold can be changed according to the value of said register.

5. The blood glucose measurement system according to claim 1,
wherein the controller outputs the non-invasive actuation signal on the basis of a preset non-invasive measurement cycle.

6. The blood glucose measurement system according to claim 5,
wherein the controller comprises a register that can be written to from the outside, and the non-invasive measurement cycle can be changed according to the value of said register.

7. The blood glucose measurement system according to claim 1,
wherein the non-invasive blood glucose measurement apparatus comprises a processing status notification component that notifies the user with a processing status signal, and sends out a processing status signal that is outputted from the blood glucose level calibration calculator and indicates whether or not calibration is in progress.

8. The blood glucose measurement system according to claim 7,
wherein the processing status notification component notifies the user with sound.

9. The blood glucose measurement system according to claim 7,
wherein the processing status notification component notifies the user with light.

10. The blood glucose measurement system according to claim 7,
wherein the processing status notification component notifies the user with vibration.

11. The blood glucose measurement system according to claim 7,
wherein the processing status notification component notifies the user with a display.

12. The blood glucose measurement system according to claim 1,
wherein the invasive measurement command component instructs the user about the invasive blood glucose measurement apparatus with sound.

13. The blood glucose measurement system according to claim 1,
wherein the invasive measurement command component instructs the user about the invasive blood glucose measurement apparatus with light.

14. The blood glucose measurement system according to claim 1,
wherein the invasive measurement command component instructs the user about the invasive blood glucose measurement apparatus with vibration.

15. The blood glucose measurement system according to claim 1,
wherein the invasive measurement command component instructs the user about the invasive blood glucose measurement apparatus with a display.

16. The blood glucose measurement system according to claim 1,
wherein the blood glucose measurement information is the blood glucose levels measured with the blood glucose level measurement component and the timing at which these measurements were made.

17. The blood glucose measurement system according to claim 1,
wherein the blood glucose level estimator replaces the value of the non-invasive blood glucose threshold with the value of the invasive blood glucose threshold when the amount of change in a blood glucose level measured with the invasive blood glucose measurement apparatus from a time of 0 minutes has reached or exceeded the non-invasive blood glucose threshold.

18. The blood glucose measurement system according to claim 17,
wherein the blood glucose measurement information includes the blood glucose level measured with the blood glucose level measurement component, the timing at which these measurements were made, and the temperature at which these measurements were made.

19. The blood glucose measurement system according to claim 17,
wherein the blood glucose level estimator comprises a register that can be written to from the outside, and the function of replacing the non-invasive blood glucose threshold with the invasive blood glucose threshold can be switched on or off according to the value of said register.

20. The blood glucose measurement system according to claim 1,
wherein the invasive blood glucose measurement apparatus further has an invasive blood glucose level display component that displays the blood glucose level measured by the blood glucose level measurement component,
the invasive blood glucose level display component notifies the user of the blood glucose level measured by the blood glucose level measurement component, and
the blood glucose level calibration calculator calculates calibration data on the basis of the blood glucose level inputted by the user and the estimated blood glucose level found by the blood glucose level estimator.

21. The blood glucose measurement system according to claim 20,
wherein the invasive blood glucose level display component notifies the user with sound.

22. The blood glucose measurement system according to claim 20,
wherein the invasive blood glucose level display component notifies the user with light.

23. The blood glucose measurement system according to claim 20,
wherein the invasive blood glucose level display component notifies the user with vibration.

24. The blood glucose measurement system according to claim 20,
wherein the invasive blood glucose level display component notifies the user with a display.

25. The blood glucose measurement system according to claim 1,
wherein the invasive blood glucose measurement apparatus automatically begins measuring the blood glucose level according to a command from the invasive measurement command component of the non-invasive blood glucose measurement apparatus.

26. The blood glucose measurement system according to claim 1, wherein the controller outputs the invasive actuation signal when a specific length of time has elapsed since the blood glucose level was measured by the invasive blood glucose measurement apparatus even if the amount of change in the estimated blood glucose level has not reached or exceeded the preset non-invasive blood glucose threshold.

27. The blood glucose measurement system according to claim 26, wherein the controller comprises a register that can be written to from the outside, and the specific length of time can be changed according to the value of said register.

28. The blood glucose measurement system according to claim 1, wherein the controller outputs the invasive actuation signal when measurement has been repeated a specific number of times with the non-invasive blood glucose measurement apparatus since the blood glucose level was measured by the invasive blood glucose measurement apparatus even if the amount of change in the estimated blood glucose level has not reached or exceeded the preset non-invasive blood glucose threshold.

29. The blood glucose measurement system according to claim 28, wherein the controller comprises a register that can be written to from the outside, and the specific number of times can be changed according to the value of said register.

30. The blood glucose measurement system according to claim 1,
wherein the controller outputs the invasive actuation signal when the difference between the estimated blood glucose level and the blood glucose level measured by the invasive blood glucose measurement apparatus after calibration has reached or exceeded an abnormal blood glucose threshold.

31. The blood glucose measurement system according to claim 30,
wherein the blood glucose level estimator comprises a register that can be written to from the outside, and the abnormal blood glucose threshold can be changed according to the value of said register.

32. The blood glucose measurement system according to claim 1,
wherein the controller counts the number of times that the amount of change in the estimated blood glucose level after calibration has continuously reached or exceeded an abnormal blood glucose threshold, and outputs the invasive actuation signal when the continuous number of abnormal states has reached or exceeded a continuous abnormal state threshold.

33. The blood glucose measurement system according to claim 32,
wherein the blood glucose level estimator comprises a register that can be written to from the outside, and the continuous abnormal state threshold can be changed according to the value of said register.

34. A non-invasive blood glucose measurement apparatus in which a measured non-invasive blood glucose level is calibrated using a blood glucose level measured with an invasive blood glucose measurement apparatus that collects blood from the body and measures the blood glucose level on the basis of an invasive measurement command, the non-invasive blood glucose measurement apparatus comprising:

- a controller that outputs a non-invasive actuation signal that instructs the non-invasive blood glucose measurement apparatus to detect a characteristic quantity in the body, and an invasive actuation signal that instructs the invasive blood glucose measurement apparatus to begin measuring a blood glucose level;
- a characteristic quantity detector that detects the characteristic quantity in the body on the basis of the non-invasive actuation signal;
- a blood glucose level estimator that finds an estimated blood glucose level on the basis of the characteristic quantity detected by the characteristic quantity detector and calibration data;
- a blood glucose level calibration calculator that calculates calibration data from the blood glucose measurement information, including blood glucose levels, measured by the invasive blood glucose measurement apparatus, and the estimated blood glucose level found by the blood glucose level estimator; and
- an invasive measurement command component that receives the invasive actuation signal outputted from the controller and instructs the invasive blood glucose measurement apparatus to measure the blood glucose level, wherein the controller outputs the invasive actuation signal when the difference between the estimated blood glucose level and the blood glucose level measured by the invasive blood glucose measurement apparatus during calibration has reached or exceeded a preset non-invasive blood glucose threshold.

* * * * *